United States Patent [19]

Byler et al.

[11] Patent Number: 5,514,973
[45] Date of Patent: May 7, 1996

[54] SYSTEM FOR ANALYZING MOISTURE CONTENT OF MATERIALS SUCH AS COTTON

[75] Inventors: Richard K. Byler, Stoneville; William S. Anthony, Greenville, both of Miss.

[73] Assignee: The United States of America as represented by the Secretary of Agriculture, Washington, D.C.

[21] Appl. No.: 273,244

[22] Filed: Jul. 11, 1994

[51] Int. Cl.⁶ .................................................. G01N 27/12
[52] U.S. Cl. .......................... 324/695; 324/694; 324/722; 73/73; 364/482
[58] Field of Search ..................... 324/693, 694, 324/695, 721, 722; 73/73; 364/482

[56] References Cited

U.S. PATENT DOCUMENTS

| | | | |
|---|---|---|---|
| 2,063,840 | 12/1936 | Fairchild et al. | 175/183 |
| 3,005,154 | 10/1961 | Moore et al. | 324/65 |
| 3,370,360 | 2/1968 | Smith | 34/48 |
| 4,266,188 | 5/1981 | Thompson | 324/695 |
| 4,584,522 | 4/1986 | Varela | 73/73 X |
| 4,868,491 | 9/1989 | Black | 324/694 |
| 5,087,120 | 2/1992 | Anthony | 356/36 |
| 5,125,279 | 6/1992 | Anthony et al. | 73/866 |
| 5,218,309 | 6/1993 | Nelson et al. | 324/664 |

OTHER PUBLICATIONS

Byler, "Resistance–Moisture Content Relationship for Cotton Lint", (1992 Proceedings Beltwide Cotton Conference; pp. 1389–1391), 1992.
Byler, "Cotton Lint Moisture Measurement and Control in the Gin", (Amer. Soc. Ag. Eng., Paper No. 923032; Jun. 1992).

*Primary Examiner*—Kenneth A. Wieder
*Assistant Examiner*—Glenn W. Brown
*Attorney, Agent, or Firm*—M. Howard Silverstein; Joseph A. Lipovsky; John D. Fado

[57] ABSTRACT

A system for analyzing the moisture content of bulk cotton or other non-homogeneous flowable solid substrates comprising: an electrical sensor consisting of multiple electrically independent measuring electrodes, each of which independently measures the moisture content of different portions of the sample; a means of pressing the mass against the surface of the sensor to form a face of uniform substrate density on that part of the mass which is pressed against the sensor; means for analyzing such face for moisture content; and a means for releasing the pressure on the halted mass to allow it to resume movement.

19 Claims, 5 Drawing Sheets

SYSTEM FOR ANALYZING MOISTURE CONTENT OF MATERIALS SUCH AS COTTON

FIELD OF THE INVENTION

The present invention relates to analyzing the moisture content of non-homogeneous flowable materials, such as cotton, as it is being processed.

BACKGROUND OF THE INVENTION

The goal of ginning is to produce a high quality product for the mills at a profit for the gin. The quality of the lint produced by a gin is dependent on the initial seed cotton quality and on the type and degree of cleaning and drying performed at the gin plant. Both the efficiency of the cleaning machines and damage done to the cotton fibers during cleaning and ginning are strongly influenced by the fiber moisture content during processing (Mangialardi and Griffin; 1977; Restoring Moisture to Cotton at Midsouth Gins; USDA Technical Bulletin No. 1553). Griffin (1977; *Cotton Ginners Handbook*. USDA Handbook No. 503, pp. 13–17) reported that the moisture content of cotton lint should be in the range of 6.5 to 8 percent to maintain optimum fiber quality. In order to maintain a lint moisture in this range the drying equipment needs to be adjusted due to changes in ambient air and in the initial lint moisture content. Proper adjustment of the drying system cannot be made without measuring the moisture content of the dried lint.

At present, annual cotton production in the United States is approximately 14 million bales; with these being processed by 1600 domestic cotton gins. Accurate measurement of moisture content during gin processing will bring about a fuel savings of $0.50 per bale while simultaneously realizing a value improvement of approximately $10 per bale due to the reduction in fiber damage caused by excessive moisture reduction.

In commercial resistance moisture meters all the electrode arrays are connected in series, parallel, or a combination of series and parallel. The resistance measurement of each individual electrode array is relatively high. If these measurements are connected in series, the total resistance of the circuit soon becomes so large that the resistance cannot be measured with currently available techniques. If the number of electrode arrays requisite for a statistically significant sample are used, it is not possible to measure in series their cumulative resistance accurately enough to obtain a reliable moisture reading.

If the resistances are connected in parallel the resulting resistance is a nonlinear representation of all of the measured resistances. This total resistance is smaller than the individual resistances so it can be accurately measured, however, the nonlinear combination of the individual sample resistances disproportionately emphasizes the smaller resistances and biases the representative resistance.

In addition, the relationship between resistance and moisture content is nonlinear. When the resistance is converted to moisture content by means of linearizing equations or linearizing electronics the smaller resistances are given more weight in determining the mean during calibration, skewing the relationship in the same direction as the parallel resistance combination does, thereby exacerbating the problem. In the application of traditional measurements and analysis, the variation in moisture which naturally occurs in the samples is treated in such a way that the results are skewed, resulting in lowered accuracy. Additionally, commercial sensors do not correct for large differences in resistance caused by changes in the temperature of the sensor or the temperature of the solid.

Resistance has been used to measure the moisture content of agricultural materials for many years and a number of related publications have been published. Fairchild et al., U.S. Pat. No. 2,063,840 disclose a moisture testing device for various kinds of material including cotton based on measuring electrical resistance. Multiple electrodes which are electrically in common are used. Means are provided to compress the tested material about the electrode to such a degree that a large and uniform area of contact between the electrodes and the material may be established for successive samples. The use of sample temperature compensation, pressure indication and the determination of resistance/moisture relationships are discussed.

Moore et al., U.S. Pat. No. 3,005,154 discloses moisture testing systems based on electrical resistance and relates to problems presented by ascertainment of a single resistance value based on a plurality of electrical paths through the test material. This is done primarily for the purpose of obtaining an approximation of the average moisture content of plural bodies or samples of material.

Smith, U.S. Pat. No. 3,370,360 discloses an apparatus for analyzing moisture content of materials including cotton having contact electrodes for resistance measurement. A number of parallel electrodes may be utilized so as to contact a large number of random pieces of material. A pulse generator produces electrical pulses at a frequency controlled by the resistance between electrodes. The pulses are produced by the charge and discharge of the capacitor.

Mangialardi et al. (USDA, ARS Prod. Res. Report No. 128; 1971) describe several electrode configurations for continuous measurement of cotton moisture incorporated into roller systems. Employment of large electrode areas was found to cause decreases in resistance greater than what could be attributed to area alone. Their explanation for this behavior was that electrical current seeks the path of least resistance (i.e., the dampest cotton). The greater the electrode area; the greater the chance of including damp cotton in the measurement.

Anthony, U.S. Pat. No. 5,087,120 discloses a system for analyzing entrained solids such as cotton for properties selected from the group consisting of color, trash content, moisture content and combinations thereof. A pressing means in the form of a rotatable plate is taught that presses the mass to be measured against an interior conduit surface to form a face of uniform cotton density that may be analyzed for such properties. Resistance devices are referenced for moisture measurement.

Anthony et al., U.S. Pat. No. 5,125,279 disclose an alternate system to that shown in U.S. Pat. No. 5,087,120 for the same purpose of analyzing entrained solids such as cotton for properties selected from the group consisting of color, trash content, moisture content and combinations thereof. The pressing means taught is in the form of a retractable ram that presses the mass to be measured against an interior conduit surface to form a face of uniform cotton density that may be analyzed for such properties.

Nelson et al., U.S. Pat. No. 5,218,309 disclose means for non-destructively measuring the moisture content of singular agricultural products by use of a parallel plate electrode assembly to measure at least two independent parameters of complex electrical impedance or admittance.

Byler (1992 *Proceedings Beltwide Cotton Conference,* pp. 1389–1391; and ASAE Paper No. 923032; June 1992) describes equations for the determination of cotton moisture content from resistivity measurements.

SUMMARY OF THE INVENTION

We have now developed an improved system of resistivity based moisture measurement for flowable materials such as cotton. Generally, the invention comprises methods and apparatus for measuring multiple resistances from product subsamples that discard discrepant readings, caused by product contaminants, that fall outside of preset parameters and using the mean of the remaining readings as the basis of determining measured moisture content. Material temperature is optionally measured and its effect on resistance is compensated for. This procedure avoids combining the resistances of the smaller samples, but combines the individual moisture readings. Accuracy of resistance moisture measurement was found to be related to the size of the measured sample, with larger samples producing more accurate readings. Any larger sample can be considered to be made up of several smaller samples interconnected in some specific way, determined by the geometry of the sample holder.

The present invention requires the cotton to be compressed, so as to present a face of uniform cotton density to the moisture measuring system. In the case of lint or seed cotton, the degree of pressing or compression is such that the mass of halted cotton presents a face of uniform cotton density on that part of the mass which is pressed against the sensor wherein the uniform density is sufficient to enable the resistance of the mass to be accurately analyzed and converted to moisture content using a unique array of sensors.

Ordinarily, the system is carried out in an intermittent or cyclic manner, so that a different mass of cotton, but a mass of essentially the same density each time, is pressed against said sensor. After compression, the pressure is removed, and the sample is removed and replaced with another or, in the case of an intraconduit sensor system, the sample is allowed to resume its pathway through the conduit.

As used in the specification and claims, the phrase "a face of uniform cotton density," in reference to the mass of cotton being pressed against said sensor, means that the face of the mass which is pressed against the surface essentially is filled with cotton and impurities, with no voids. In other words, the sample is sufficiently compressed so that its flattened face essentially is completely occupied by cotton and impurities. This enables the sensor adjacent to the flattened face to make an analysis of moisture content thereof.

In the case of a cotton gin, the cotton may be rapidly passing through the conduit, in an upward, downward, or lateral direction. Material velocities in these systems are often 1000–5000 or more feet per minute, but include scenarios involving free-fall speeds, or static conditions. The device may be incorporated into any duct, pipe, or chamber in a gin or in a textile mill, or a cotton harvester, or in a laboratory. It may also be used as part of the static cotton analysis system such as that referred to as a high volume instrument classification system which is used by the Agricultural Marketing Service (AMS) of the United States Department of Agriculture (USDA), to measure the strength, length, micronair, uniformity, color and trash of cotton. Accurate measurement of the moisture content during classification of cotton will allow the USDA, AMS to relax the conditioning requirements for cotton before classification which will lower their costs and will improve the accuracy of the strength measurement of cotton fiber.

An object of the instant invention is to provide a system for measuring the moisture content of a non-homogeneous flowable material in a harvesting, storage or processing system.

Another object of the present invention is to provide a system for measuring the moisture content of cotton during harvest, storage, ginning, classification, textile processing, or fabric processing.

Yet another object is to provide an apparatus for analyzing solids such as flowable particulate matter, including seeds, waste, natural and man-made fibers, pharmaceuticals, wood products, and so forth.

Still another object is to provide data that may be employed to automatically or manually adjust drying and cleaning variables, so as to improve the final product.

Yet further, an object is to provide means of analyzing cotton as it is travelling through a conduit at low or high speeds in a gin or textile mill, without removing it from the conduit.

A still further object is to provide portable and easily adaptable analysis equipment for any gin configuration or cotton analysis system.

An even further object is to provide moisture content of cotton continuously as it is processed.

A further object is to measure the moisture of mixtures of cotton and synthetics in textile processing plants.

Other objects and advantages will be obvious from the following more detailed description of the invention.

DETAILED DESCRIPTION OF THE DRAWINGS

Figure 1A:
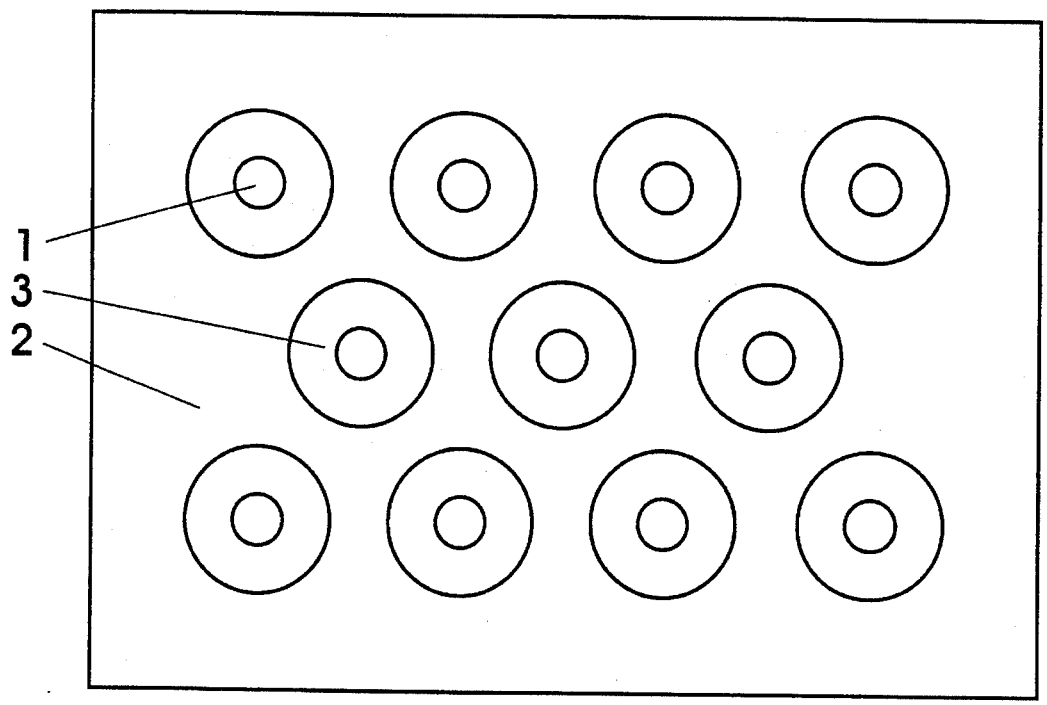

FIG. 1*a* is an elevation view of an electrode array of the invention.

Figure 1B:
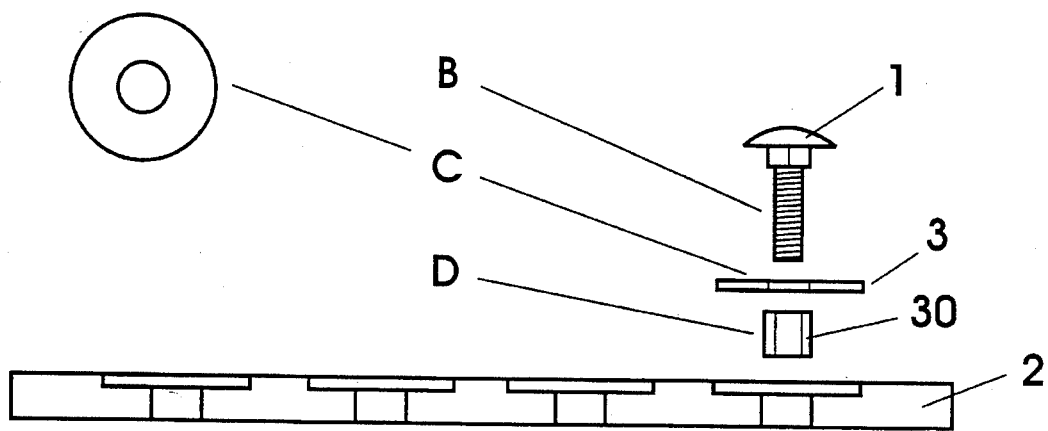

FIG. 1*b* is a cross-sectional elevation view of the electrode array of FIG. 1*a*.

Figure 2:
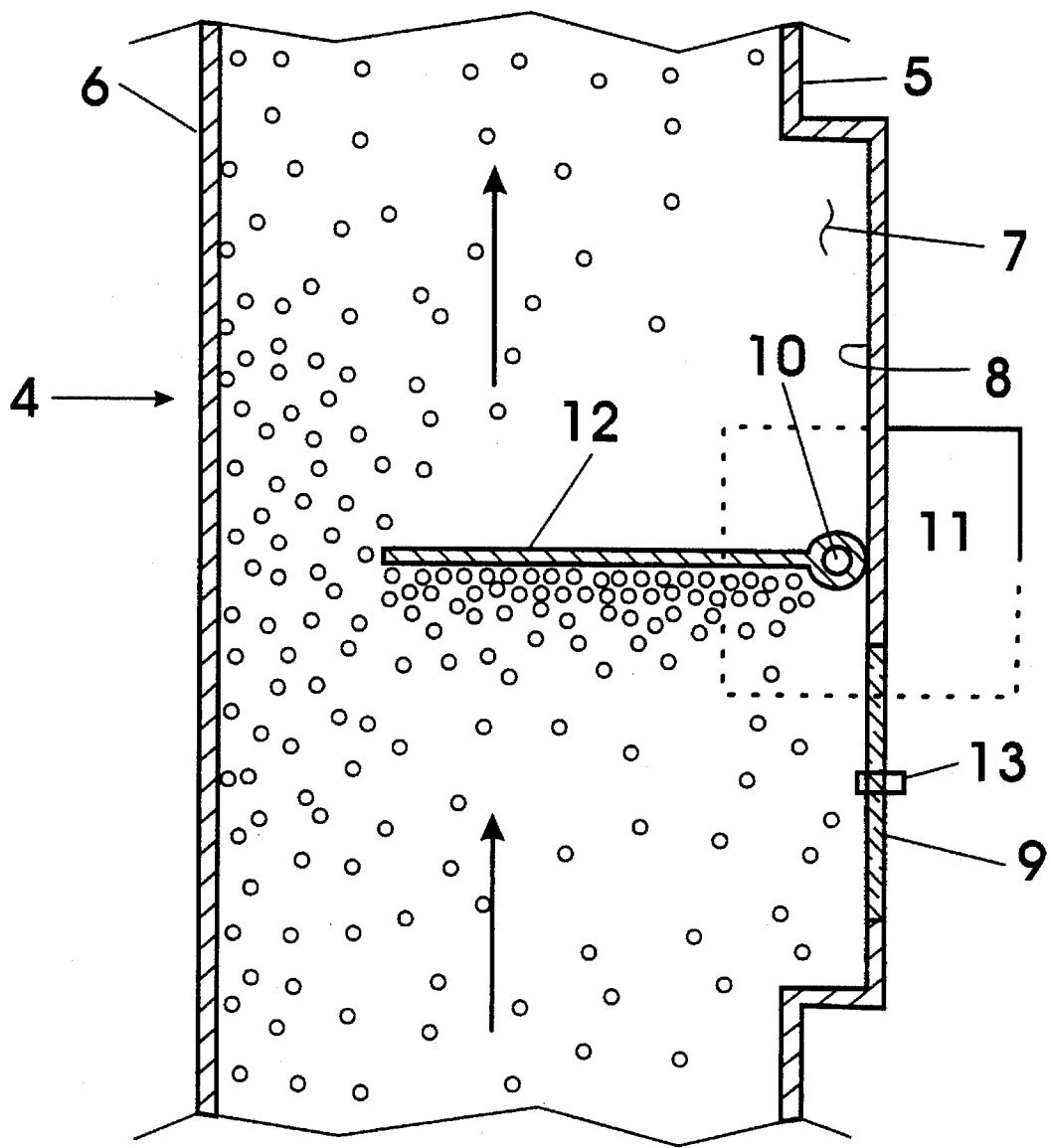

FIG. 2 shows a side sectional view of an electrode array in conjunction with a rotating plate sampling device.

Figure 2A:
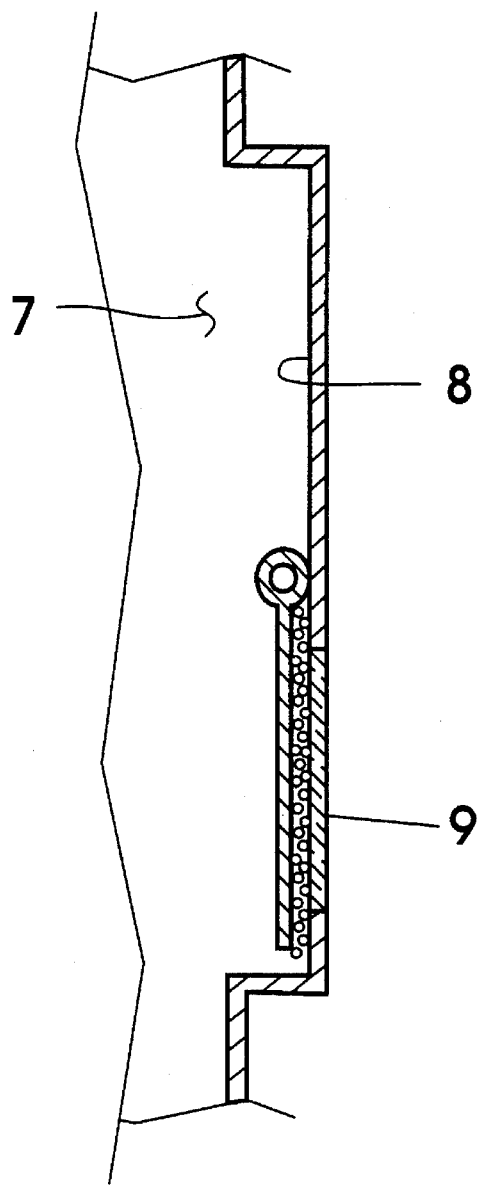

FIG. 2*a* shows the rotating plate of FIG. 2 in the closed position.

Figure 2B:
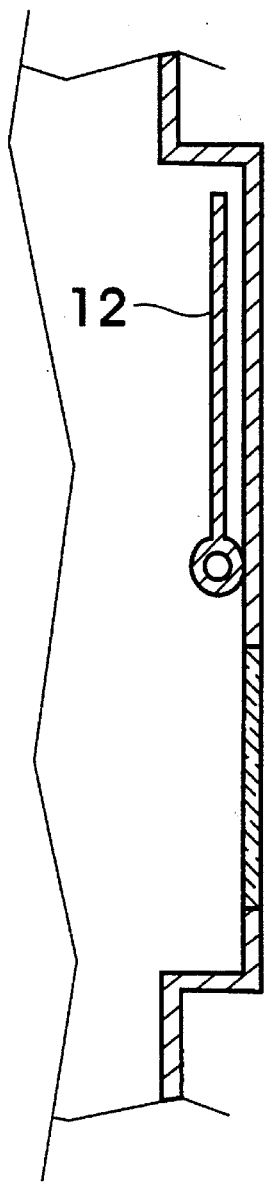

FIG. 2*b* shows the rotating plate of FIG. 2 in the open position.

Figure 3A:
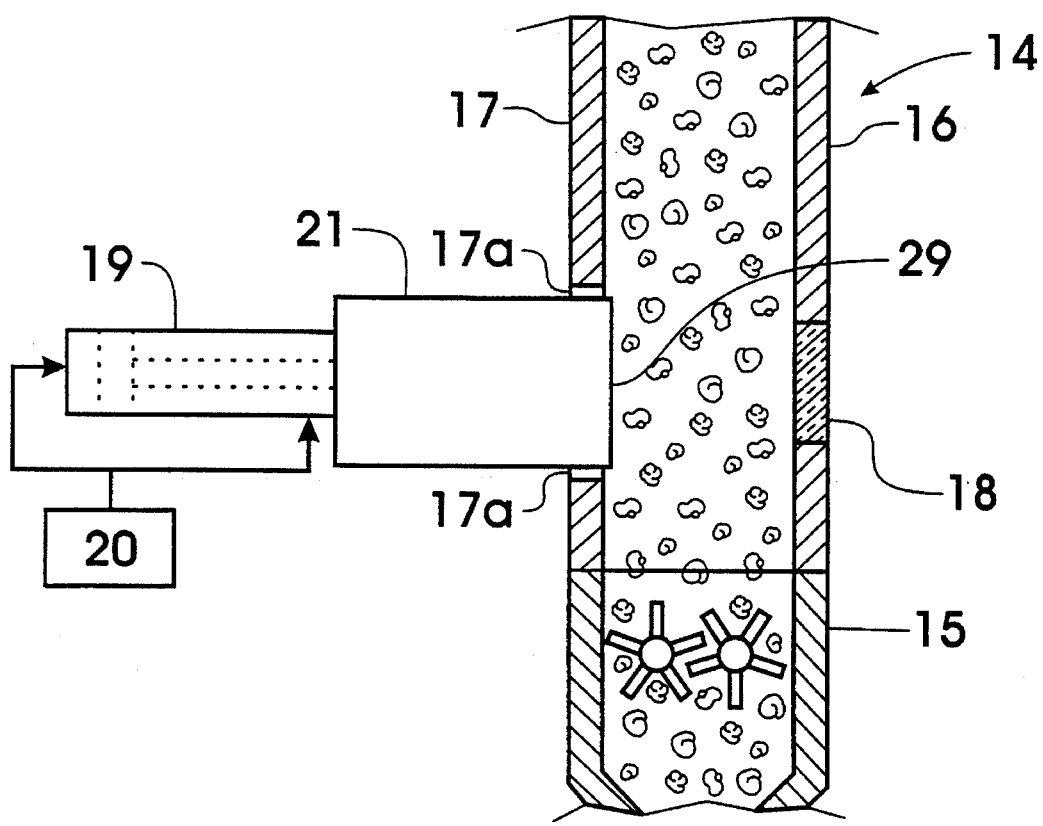

FIG. 3*a* shows a side sectional view of an electrode array in conjunction with a retractable ram sampling device.

Figure 3B:
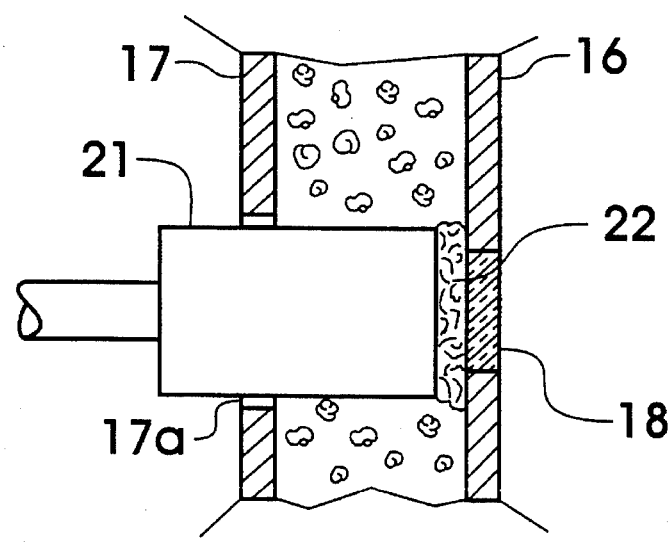

FIG. 3*b* shows the retractable ram of FIG. 3*a* in the closed position.

Figure 4:
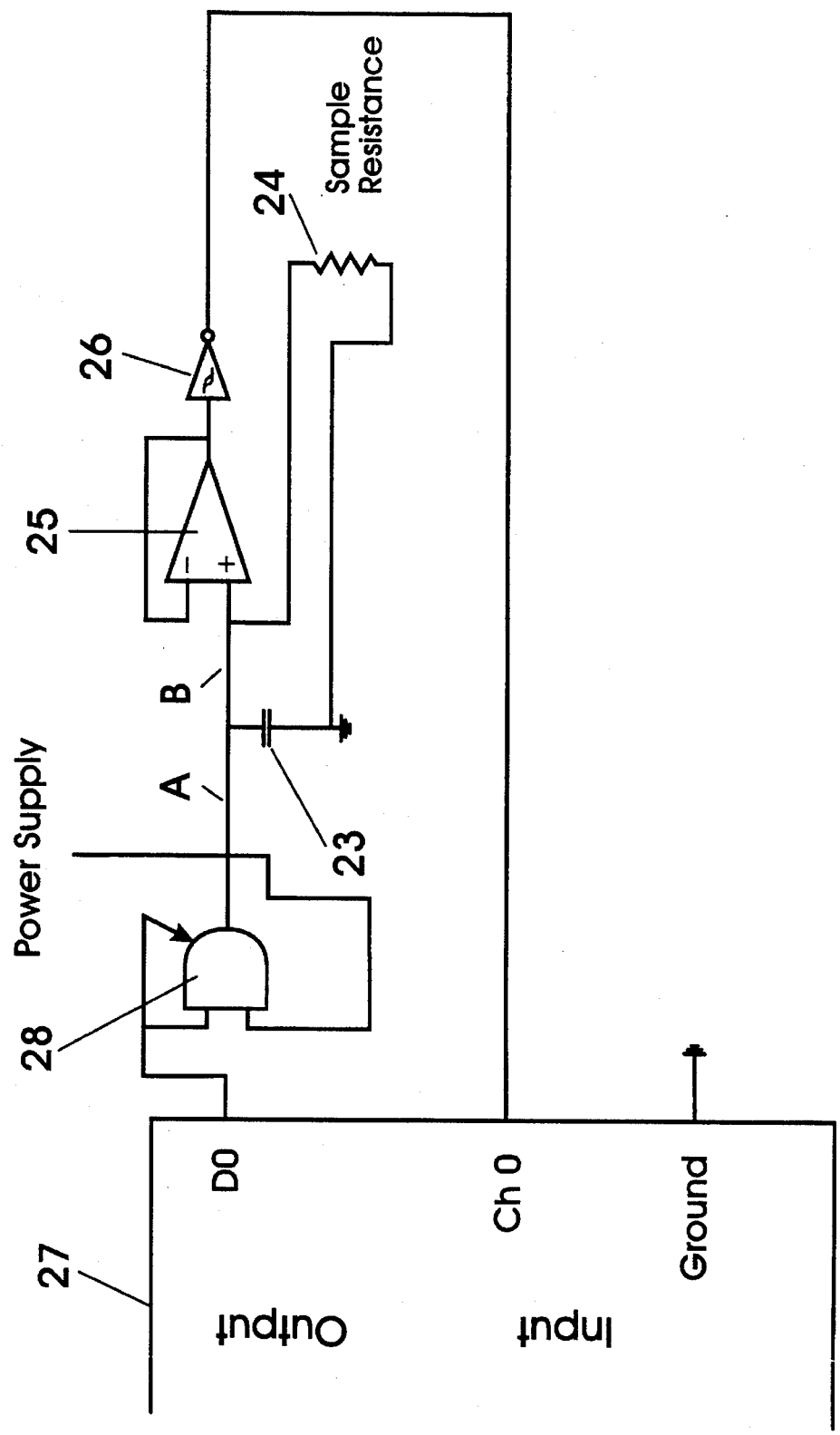

FIG. 4 shows typical electronic circuitry used in conjunction with the electrode measuring elements.

DETAILED DESCRIPTION OF THE INVENTION

The invention may be beneficially employed for the moisture measurement of agricultural products including cotton as well as other non-homogeneous solids. Such solids are defined as those which, due to natural variation or the non-uniform entrainment of contaminating matter, resistance measures of different samples of the same material may vary by 1% or more. This situation is common with flowable agricultural products such as grains (e.g., corn, wheat, rice, oats, etc.), legumes, such as soybean and peanuts, seeds, nuts, and cellulosic products such as wood chips and cotton. Flowable products are defined as those which while solid are of such a particulate nature that they are amenable to harvest, transport and processing in a continuous manner due to their possession of gross general flow characteristics. Due to modern techniques of mass harvesting, it is common for entrainment of particulate matter such as soil, and undesired plant parts (e.g., leaves, stems, seed hulls, etc.) in the harvested material. Details of the invention will be described with regard to processing cotton, although it may be similarly employed for other solids.

The instant invention employs a plurality of electrically independent measuring electrodes, optionally sharing an electrically common reference potential electrode, which are used for the simultaneous gathering of multiple independent resistivity measurements from a tested sample. The electrodes are constructed of a highly conductive material such as copper, aluminum, or stainless steel and are of a physical configuration such that their material contact surfaces will not entrain the tested material after testing is complete. Envisioned configurations include the embedding of electrodes in a surface, such that their contact surface is continuous with such, or the use of an electrode with a smoothly curved material contact surface. With such designs the measured material will not become entrained by the electrodes and require manual cleaning and removal between tests. The electrodes may be present in the form of multiple electrically and physically independent electrode pairs. In a preferred embodiment however one electrode of each of the pairs is electrically common. In FIG. 1a a plan view of a preferred embodiment for such electrode measuring means is shown in which reference numeral 1 designates one of a plurality of measuring electrodes which are insulatively isolated from both each other and a common reference potential electrode 2 by means of a non-conductive washer 3. A cross-sectional elevation of FIG. 1a is represented in FIG. 1b wherein a non-conductive spacer 30 is shown which prevents electrical contact between the base of measuring electrode 1 and the common reference potential electrode 2. The voltage between the measuring electrode 1 and the reference potential electrode 2 may be whatever value is sufficient to create a measurable reading. The envisioned range is from about 3 V to about 100 V. A second design parameter in the electrode arrays is the separation distance between the reference electrode 2 and the measuring electrode 1. This distance should be sufficiently large so as to provide sufficient sample size and to prevent the corruption and subsequent culling of an excessive number of individual resistivity measures caused by the presence of contaminating matter that either bridges or blocks the electrical path between the electrodes; but not so large as to create unmeasurably large resistances. In the case of cotton measurement this distance will range from about 0.05 inch to about 0.5 inches. The number of measuring electrodes that may be used in this array has no physically required upper limit, but due to situational and cost constraints typically will range from 2 to about 100, preferably from about 3 to about 20. In the case of cotton a most preferred range is from about 5 to about 9 measuring electrodes. While FIG. 1a and FIG. 1b represent the measuring electrodes as round, they may possess alternate geometries such as being linear. Dimensions of the array are not critical, only needing to satisfy situational requirements (e.g., the number of electrodes needed and the physical limitations of the area into which it is being placed. Typical planar dimensions of the array range from about 2 inches to about 8 inches high, and from about 4 inches to about 20 inches wide.

Consistent and repeatable measurement of material resistivity requires that a face of uniform density of the tested material is placed in contact with the electrode array. Pressures of about 1 to about 6 psi on the surface of the electrode array are suitable for sufficiently compressing cotton so as to provide a cotton face of uniform density. In these instances the face of the cotton mass will typically experience a pressure of about 2 psi; and the mass will ordinarily be compressed to a thickness of about 0.5 inch.

The particular means of sample compression is not critical. The electrode array may be used in conjunction with known sample capture and compression means such as those taught by Anthony in U.S. Pat. No. 5,087,120 and Anthony et al. in U.S. Pat. No. 5,125,279; both teachings of which are herein incorporated by reference. These patents are directed to apparatuses that operate within the material flowstreams of cotton processing plants for the purpose of providing samples which present a face of uniform cotton density against a measuring surface used to analyze for properties including moisture content. Sample compression may be achieved by other, including manual, means.

An embodiment of the instant invention is shown in FIG. 2 wherein reference numeral 4 designates a typical rectangular duct in a ginning system, wherein the cotton is travelling upwardly toward, for example, a lint cleaner. The cotton usually is moving rapidly at speeds of about 1000–5000 feet per minute, typically about 1500 feet per minute for lint cotton, and about 4500 feet per minute for seed cotton.

Reference numerals 5 and 6 designate the front and back walls of duct 4. The distance therebetween, or duct depth, typically is about 4–8 inches in the case of a lint duct; while full scale width typically is about 48–96 inches. For seed cotton, round ducts, having a diameter of about 12–24 inches, normally are used.

Provided in wall 5 is a recess 7. At the back of the recess is a surface 8 having an electrode array 9 therein. Positioned within the recess is a rotatable shaft 10 driven by a rotary actuator assembly 11. Rigidly attached to, or integral with shaft 10 is a plate or baffle 12, that is positioned in its solids-capturing or -halting mode in FIG. 2, i.e., the baffle projects transversely into the duct. FIGS. 2a and 2b illustrate the pressing and retracted-position modes, respectively, of plate 12. In these latter positions, plate 12 is positioned totally within recess 7 so as not to cause flow obstruction to cotton passing through the duct during compression or retraction. As can be seen from both FIGS. 2a and 2b, substantial quantities of the flowable solids, such as cotton, bypass plate 12 during the capturing and pressing steps, and pass through the duct without being halted. Only a small percentage of the cotton usually will be halted, displaced, and pressed against electrode array 9, in comparison to the total volume of cotton travelling through duct 4. In many instances, over 90% of the cotton will pass through the duct without analysis.

Typical dimensions of plate 12, are about 6 inches high, and about 10 inches wide regardless of duct width. For such plate dimensions, shaft 10 typically will be at least 1 inch in diameter, and will extend the entire width of the duct. For a duct width of 60 inches, a shaft having a diameter of 1½ inches is suitable. To assure that compressed cotton totally covers the electrode array 9, the array should be slightly smaller than the plate so that the plate overlaps the array boundary by about 1 inch. The plate, which may be solid or perforated, may be constructed of any suitable material including metal such as stainless steel or aluminum.

Generally speaking, hydraulics, pneumatics, or electric motors may be employed to activate rotary actuator assembly 11, pneumatics being preferred. In most instances, pressures of about 1 to 6 psi are suitable for sufficiently compressing the cotton so as to provide a cotton face of uniform density at electrode array 9. Under such pressure, the face of the cotton mass typically will experience a pressure of about 2 psi; and the mass ordinarily will be compressed to a thickness of about 0.5 inch.

Conventional heavy duty rotary actuator air cylinders capable of operating at 250 psi maximum are suitable for achieving such compression. Appropriate pneumatic hardware, including air control valves, solenoids, air supply, and related equipment will be obvious to those skilled in the art.

As to the details of rotary actuator assembly 11, it may include conventional catalogue hardware. Typically, the actuator transfers the linear motion of a hydraulic cylinder into a high torque rotary motion. Air pressure applied to a set of cylinders internally connected to a gear rack causes the rack to move back and forth. The rack engages a pinion gear which in turn rotates the pinion output shaft assembly in a predetermined rotational increment, in the present case being 180°. Integral flow controls provide rotational speed adjustment. Employing a 1½ inch bore shaft, inlet air pressures of about 60–80 psi provide torque outputs of 84–112 pounds, respectively. Dayton "Speedaire" model 2A121 is an exemplary pneumatic rotary actuator.

During operation, each cotton mass being analyzed at electrode array 9 is forced to pause a brief time, typically less than 2 seconds, to be analyzed before resuming its passage through duct 4.

Measurement of the material by the plurality of electrically independent measuring electrodes is carried out in a substantially simultaneous manner whereby each electrode base signal is generated and collected in the same time frame, no greater than 5 seconds, preferably being about 1 second or less.

In an alternate embodiment the electrode array may be located on plate 12 thereby allowing additional sensors (e.g., color or trash) to be installed in the recess of the duct. A pressure sensor 13 may be installed so as to indicate when sufficient density is achieved to ensure correct resistance readings.

Another embodiment of the invention utilizing a compression ram is shown in FIG. 3a and FIG. 3b.

In FIG. 3a, reference numeral 14 designates a typical holding chute or hopper in a ginning system, wherein the chute passes bulk cotton to, for example, the feeding element 15. The cotton moves downward through the chute, usually at a speed of a few feet per minute, typically 3–5 feed per minute. Chute dimensions, in the case of a "feed control" holding chute, typically are 4–16 feet high, 4–12 feet wide, 1–4 feet deep. Other holding chutes, e.g., the hopper for an extractor-feeder, may have the following dimensions: 1–4 feet high, 4–12 feet wide, 1–3 feet deep. Similar chutes exist in textile mills.

Reference numerals 16 and 17 designate first and second opposing walls or surfaces, preferably the front and back walls of the chute, wherein the distance there between may be about 1–4 feet, typically about 2 feet, in the case of a feed control holding chute. Wall 16 may include a electrode array 18 or the electrode array can be mounted at 29 on the face of the compression ram cylinder.

Adjacent to wall 17 at opening 17a, directly opposite electrode array 18, is a conventional piston-cylinder assembly illustrated by reference numeral 19 fixed to a frame member (not shown), supplied with fluid pressure from a source 20. The assembly is connected to a ram 21 that intermittently or cyclically displaces cotton from its downward pathway and compresses the displaced cotton against the electrode array 18.

The length of the assembly 19 must be sufficient to permit ram 21 essentially to traverse the distance between walls 16 and 17, so as to push a small mass of cotton 22 against electrode array 18 when fully extended, as illustrated in FIG. 3b.

Ram 21, which may be constructed from a hollow metal cylinder, has a length greater than the distance between walls 16 and 17. This assures that at least a part of the ram still is lodged in opening 17a even when fully extended. In this manner, no cotton will be trapped behind the ram during its retraction stroke. In addition, by maintaining at least part of the ram within opening 17a during the entire operation, support continuously is provided for the ram.

Hydraulics or pneumatics may be employed to activate assembly 19, pneumatics being preferred. In most instances, pneumatic pressures of about 75 to 150 psi are suitable for sufficiently compressing the cotton so as to provide a cotton face of uniform density at electrode array 18. Under such pressure, the face of the cotton mass typically will experience a pressure of about 2 psi; and the mass ordinarily will be compressed to a thickness of about 2 inches.

Conventional heavy duty, double-acting air cylinders capable of operating at 250 psi maximum are suitable for achieving such compression. Appropriate pneumatic hardware, including air control valves, solenoids, air supply, and related equipment will be obvious to those skilled in the art.

As to dimensions, a diameter of about 6–8 inches is suitable for ram 21 driven by a 1½–2 inch (diameter) pneumatic piston, whereby a small mass of cotton will be displaced and pressed against electrode array 18 in comparison to the total volume of cotton travelling through chute 14.

During operation, each cotton mass being analyzed at electrode array 18 is forced to pause a very brief time, typically less than 2 seconds, to be analyzed at the electrode array 18, before resuming its downward passage through holding chute 14. A substantial amount of the cotton passing through the chute, e.g., at least 30% is not displaced towards the analyzer, and passes through the chute without compression or analysis. In many instances, over 90% of the cotton will pass through the holding zone without analysis.

Moisture measurements may be made in a portable device wherein the sensor is mounted on a plate and material samples such as cotton are presented by hand. Compression of the sample may be accomplished without the aid of pneumatics, hydraulics or mechanical actions as long as sufficient pressure is applied.

Off-the-shelf electronic time delay relays may be used to trigger the analyzing instruments to take readings, only when compression of the cotton mass is at its maximum. For example, a relay with a timing range of 0.1 to 1.0 seconds may direct the compression cycle to start. The timer electrically may signal a directional solenoid air valve which further signals the pneumatic cylinder to activate. An electrical signal is sent to the computer by the relay about the same time as the piston is directed to extend to define the precise time for the computer to take a reading. Sufficient time is allowed for the piston to fully extend before the timer directs the cylinder to return. This time, typically 1 second, is used to delay the analyzer's computer from taking its reading until full extension occurs. If full extension of the piston is not achieved before the preset time delay occurs such as when the hold chute is fully filled with cotton, the piston remains partially extended for the full time to permit analysis before it retracts.

Independent resistance measures are collected from each measuring electrode and delivered to a signal processing means such as a computer. The resistance of the sample that is used to calculate the sample moisture content may be measured by any appropriate technique, including converting the resistance to time domain by measuring the time it takes to discharge a capacitor through the sample and converting the time to moisture content based on calibration data. For time measurement of capacitive discharge four main components are necessary. The sample with unknown resistance, a capacitor, the capacitor charging circuitry, and the circuitry to measure the discharge time. A typical circuit for this purpose is shown in FIG. 4 and consists of an integrated circuit 28 controlled by a microprocessor 27. The voltage at A goes high, charging capacitor 23 and then the charging circuitry assumes a high impedance state. The charging of the capacitor could be affected in many similar ways as long as it is charged to a repeatable voltage and the charging circuit then changes to a low current leakage path. The discharge of the capacitor should not be through the sensing amplifier 25, which needs to have high input impedance to minimize this discharge; but through the resistance being measured, 24, which is the sample of which the moisture is to be sensed. The Schmitt trigger, 26, determines when the discharge voltage is reduced to a predetermined level. The high input impedance voltage follower, 25, and level detector, 26, could be replaced by any high input impedance voltage level detector circuit.

The length of time that the voltage B is high after the charging circuit changes to the high impedance state is proportional to the resistance, 24. This time delay is measured by the timer, 27, which can be the same microprocessor which initiated the sequence, or other timing circuit. The time can then be converted to the moisture content based on a calibrated equation.

Off-the-shelf electronic time delay relays may be used to trigger the analyzing instruments to take readings only when compression of the cotton is at its maximum. The timer electronically may signal a directional solenoid air value which further signals the pneumatic actuator to activate. The time delay relay also allows a variable momentary pause after a proximity switch is activated, typically 1 second, to ensure that the computer system receives a stable reading before the assembly begins its return.

A preferred means to trigger the analyzer's computer may be provided by a pressure or force transducer 13 as shown in FIG. 2 on electrode array 9 or optionally on plate 12 that signals the computer to take a reading when adequate pressure to ensure uniform surface density is exerted on the sample.

Time delays, proportional to sample resistance, measured by timer 27 are converted to the moisture content by means of calibration equations developed by means known in the art such as those described by Byler (*American Society of Agricultural Engineers*, Paper No. 923032; June 1992 and 1992 *Proceedings Beltwide Cotton Conference*, pp. 1389–1391); herein incorporated by reference.

Calculation of the moisture content (M) may be achieved by using the equation:

$$M_n = A_n * ln(t_n) + B_n \tag{1}$$

where $M_n$=the moisture content measured by channel n, $t_n$=the time to discharge the capacitor measured on channel n, and $A_n, B_n$=coefficients determined by regression.

For applications where the temperature of the material to be tested is not constant, a material temperature sensor may be incorporated into the moisture measuring means and readings therefrom supplied to the signal processing means to adjust resistance readings for any temperature effect.

An alternate equation which may be used is:

$$M_n = A_n + (B_n - C_n/t_n)/t_n - D_n t_n \tag{2}$$

where $M_n$=the moisture content measured by channel n, $t_n$=the time to discharge the capacitor measured on channel n, and $A_n, B_n, C_n, D_n$=coefficients determined by regression After the moisture content for each channel has been determined by either eq. (1) or (2) the moisture content by channel is examined to see if it should be retained for further analysis.

The individual electrode-based moisture readings are then statistically analyzed by the signal processor and those with moisture values that fall outside preset parameters are culled. These values are readily determinable by one of ordinary skill in the art and will vary with the material being measured as well as the means by which it is being processed. One approach is to keep all readings within a certain range (e.g., those between 6.0% and 9.0%) or keep all readings within a certain range of the expected mean (e.g., 7.5±1.5%). An additional approach is to keep a running average of the mean square of the moisture readings for the different channels of the individual samples for all samples as the machine analyzes data. All points within an estimated three standard deviations of the mean of the readings for that sample would be kept and the others discarded. The mean would then be taken of the remaining data and used as the estimate of the sample moisture content.

The present invention using measurements of cotton permits the resistance based moisture determination of cotton to within ±0.3% of the air-oven value. It is to be understood that the foregoing detailed description is given merely by way of illustration and that variations may be made therein without departing from the spirit and scope of the invention. For example, individual electrodes could be paired or grouped in series or parallel to create alternate measurement configurations that could be useful in scenarios where individual sample resistance is high due to low moisture. Further, one skilled in the art would recognize that equations and formulae other than those used herein could be employed to determine the moisture content from the measured parameters.

We claim:

1. A resistivity based moisture measuring means for non-homogeneous materials comprising:

(a) a plurality of electrically independent electrode pairs, wherein one electrode of each of the electrode pairs is electrically common, resulting in a plurality of electrically independent measurement electrodes with an electrically common reference electrode for all of the measurement electrodes, and possessing non-entraining contact surfaces; and (b) signal processing means to independently review each electrode-based resistance measurement, culling those measurements which fall outside predetermined parameters, weighting, integrating and mathematically combining the signals of the remaining measurements, determining the resultant moisture content from the arithmetic mean of said remaining measurements and displaying the result.

2. The means of claim 1 further comprising a material temperature sensor which sends a signal used by said signal processing means in determining said resultant moisture content.

3. The means of claim 1 further comprising a pressure sensor for determining when adequate pressure is being applied by said non-homgeneous material to the surface of the measurement device for a valid reading.

4. The means of claim 1 wherein said signal processing means comprises a resistance-capacitance circuit and high impedance operational amp to convert resistance to a time pulse, a microprocessor based computer and software to measure time and convert the time pulse from each electrode channel to each channel's moisture, a microprocessor based computer and software to cull the unwanted readings, a microprocessor based computer and software to compute the resultant moisture content using the individual readings from the separate channels, and a microprocessor based computer to use the resulting moisture content in control, display the resulting moisture content, or communicate it with other controllers or computers.

5. The means of claim 1 comprising from about 3 to about 20 electrically independent measuring electrodes.

6. The means of claim 5 comprising from about 5 to about 9 electrically independent measuring electrodes.

7. The means of claim 1 wherein the time during which the product is pressed against the electrodes and the resistance measurement made ranges from about 0.1 to about 5 seconds.

8. The means of claim 7 wherein the time during which the product is pressed against the electrodes and the resistance measurement made is about 1 second.

9. The means of claim 1 wherein the material to be measured is an agricultural product.

10. The means of claim 1 wherein the material to be measured is cotton.

11. A method for analyzing the moisture content of flowable non-homogeneous solids comprising:
  (a) collecting multiple substantially simultaneous resistance measurements from a plurality of electrically independent measuring electrodes;
  (b) independently calculating from each electrode-based resistance measurement a moisture content measurement and culling those measurements which fall outside predetermined parameters; and
  (c) determining the moisture content of said solid by weighting, integrating and mathematically combining the remaining measurements.

12. The method of claim 11 further comprising taking a temperature measurement of said solid at the time of collecting said resistance measurements and using such to adjust said resistance measurements for temperature effects prior to determining the moisture content of said solid.

13. The method of claim 11 further comprising taking a pressure measurement of said solid to determine the appropriate time for collection of said resistance measurements.

14. The method of claim 11 wherein the material to be measured is cotton.

15. The method of claim 11 wherein the time during which the product is pressed against the electrodes and the resistance measurement made ranges from about 0.1 to about 5 seconds.

16. The method of claim 11 wherein the time during which the product is pressed against the electrodes and the resistance measurement made is about 1 second.

17. The method of claim 11 comprising collecting resistance measurements from about 3 to about 20 electrically independent measuring electrodes.

18. The method of claim 17 comprising collecting resistance measurements from about 5 to about 9 electrically independent measuring electrodes.

19. The method of claim 11 wherein said flowable solids are placed in contact with the sensor manually or robotically.

* * * * *